United States Patent
Tashiro et al.

(10) Patent No.: US 11,077,048 B2
(45) Date of Patent: Aug. 3, 2021

(54) OIL-IN-WATER EMULSION COSMETIC

(71) Applicant: SHISEIDO COMPANY, LTD., Tokyo (JP)

(72) Inventors: Mayuri Tashiro, Yokohama (JP); Yuko Nagare, Yokohama (JP); Takashi Matsui, Yokohama (JP)

(73) Assignee: SHISEIDO COMPANY, LTD., Tokyo (JP)

(*) Notice: Subject to any disclaimer, the term of this patent is extended or adjusted under 35 U.S.C. 154(b) by 0 days.

(21) Appl. No.: 16/773,142

(22) Filed: Jan. 27, 2020

(65) Prior Publication Data

US 2020/0155440 A1 May 21, 2020

Related U.S. Application Data

(62) Division of application No. 15/327,540, filed as application No. PCT/JP2014/081529 on Nov. 28, 2014, now abandoned.

(51) Int. Cl.

| | | |
|---|---|---|
| A61K 8/06 | (2006.01) | |
| A61K 8/73 | (2006.01) | |
| A61Q 17/04 | (2006.01) | |
| A61K 8/37 | (2006.01) | |
| A61K 8/81 | (2006.01) | |
| A61K 8/25 | (2006.01) | |
| A61K 8/27 | (2006.01) | |
| A61K 8/29 | (2006.01) | |
| A61K 8/41 | (2006.01) | |
| A61K 8/49 | (2006.01) | |
| A61K 8/88 | (2006.01) | |

(52) U.S. Cl.
CPC .............. *A61K 8/731* (2013.01); *A61K 8/062* (2013.01); *A61K 8/25* (2013.01); *A61K 8/27* (2013.01); *A61K 8/29* (2013.01); *A61K 8/37* (2013.01); *A61K 8/375* (2013.01); *A61K 8/41* (2013.01); *A61K 8/4966* (2013.01); *A61K 8/8158* (2013.01); *A61K 8/88* (2013.01); *A61Q 17/04* (2013.01); *A61K 2800/48* (2013.01); *A61K 2800/621* (2013.01); *A61K 2800/624* (2013.01); *A61K 2800/651* (2013.01)

(58) Field of Classification Search
None
See application file for complete search history.

(56) References Cited

U.S. PATENT DOCUMENTS

| | | | | |
|---|---|---|---|---|
| 2010/0189661 | A1* | 7/2010 | Musa | C08F 222/06 424/40 |
| 2012/0251603 | A1 | 10/2012 | Yamada et al. | |

FOREIGN PATENT DOCUMENTS

| | | |
|---|---|---|
| EP | 0 197 635 | 2/1986 |
| EP | 2 484 339 | 8/2012 |
| JP | 2007-106715 | 4/2007 |
| JP | 2007-145722 | 6/2007 |
| JP | 2009-209123 | 9/2009 |
| JP | 2010-222349 | 10/2010 |
| JP | 2012-111726 | 6/2012 |
| JP | 2012-251152 | 12/2012 |
| JP | 2013-199453 | 10/2013 |
| TW | 201125589 | 8/2011 |

OTHER PUBLICATIONS

PCT/JP2014/081529, ISR and Written Opinion dated Jan. 27, 2015, 2 pages—English, 7 pages—Japanese.
Appln. Serial No. 2017104708/15, Russian Office Action dated Sep. 14, 2018, 9 pgs.—English, 5 pgs.—Russian.
EP 14 906 718.3 German Office Action dated Jun. 18, 2019, 6 pages—English.
Perfect Essence Sunscreen A+N, by Mintel, Record ID: 2370257 published Apr. 2014, 3 pages—English , http://www.gupd.com.

\* cited by examiner

*Primary Examiner* — Jessica Worsham
(74) *Attorney, Agent, or Firm* — Andrew F. Young, Esq.; Nolte Lackenbach Siegel

(57) ABSTRACT

The present invention has the purpose of providing an oil-in-water emulsion cosmetic that contains a high quantity of an ultraviolet absorbing agent and an ultraviolet scattering agent in the oil phase and achieves a high SPF, while simultaneously having a Distinctive fresh feeling in use when applied to the skin. The present invention provides an oil-in-water emulsion cosmetic characterized by comprising (A) 0.05 to 1% by mass of a hydrophobically modified alkyl cellulose; (B) 5 to 40% by mass of an oil component; (C) 2.5 to 30% by mass of an ultraviolet scattering agent having a hydrophobic surface; and (D) a water phase thickener having low salinity tolerance; wherein the (C) ultraviolet scattering agent is dispersed in the oil phase.

4 Claims, No Drawings

OIL-IN-WATER EMULSION COSMETIC

CROSS REFERENCE TO RELATED APPLICATIONS

This application is a divisional of U.S. Ser. No. 15/327,540 filed Jan. 19, 2017, the entire contents of which are incorporated herein by reference, which relates to and claims priority as a § 371 national phase, from PCT/JP2014/081529 filed Nov. 28, 2014, the entire contents of which are incorporated herein by reference

TECHNICAL FIELD

The present invention relates to an oil-in-water emulsion cosmetic, particularly to a sunscreen cosmetic, containing an ultraviolet absorbing agent and an ultraviolet scattering agent to provide a high ultraviolet protection capability (SPF) in addition to providing a distinctively fresh feeling in use.

BACKGROUND ART

An oil-in-water emulsion cosmetic is widely used as a base material to provide a fresh feeling in use compared to a water-in-oil emulsion. However, when powders, particularly powders that have been hydrophobically treated, are blended in their inner phase (oil phase), the emulsion system tends to become unstable.

As one method of stabilizing the emulsion system, a water-soluble thickener has been applied to increase viscosity of the outer phase (water phase) of the oil-in-water base material. However, it is problematic that viscosity decrease of the water phase due to an elution of ions from the hydrophobically treated powder blended in the inner phase (oil phase) and so forth takes place and results in destabilization and causing stickiness (Patent Document 1). Patent Document 1 discloses that such elution can be prevented by strongly coating the surface of an inorganic powder.

As other stabilization methods, methods using low-viscosity oils that promote the dispersion of powder (dispersion media) or dispersing agents have been proposed. For example, Patent Document 2 describes that a hydrophobically treated ultraviolet scattering agent (zinc oxide) was stably blended into an oil phase by using a volatile oil and a liquid higher fatty acid (dispersion medium), and a silicone having a carboxyl group in the structure or sugar ester (dispersing agent).

However, (volatile) non-polar oils such as low-viscosity hydrocarbon oils or silicone oils are commonly used as dispersion media that are added for powder dispersion, and it was known that the use of polar oils in the inner phase increases the amount of distribution into the oil phase of hydrophilic groups in the surfactant and thereby makes emulsification difficult.

In other words, in order to achieve high ultraviolet protection capability, a high-polarity ultraviolet absorbing agent, and in some cases, a polar oil to serve as the solvent thereof, must be added, while also necessitating the inclusion of a non-polar oil as a dispersion medium for stably emulsifying the oil phase containing an ultraviolet scattering agent, so it was extremely difficult to suppress the total oil content while maintaining a high ultraviolet protection capability.

For example, Patent Document 3 describes that a stable emulsion was obtained by using 2-ethylhexyl 2-ethylhexanoate and/or isononyl 2-ethylhexanoate as the emulsifier in a system wherein a high-polarity ultraviolet absorbing agent, a non-polar silicone oil, and an ultraviolet scattering agent (powder) coexist. Additionally, Patent Document 4 describes an oil-in-water cosmetic having a hydrophobically treated powder stably blended into an oil phase, using a hydrophobically modified alkyl cellulose as the emulsifier. However, in these cosmetics, at least half of the oil phase (inner phase) is constituted by a non-polar oil, so there are limits to the suppression of the total oil content.

RELATED ART DOCUMENTS

Patent Documents

Patent Document 1: JP 2012-251152 A
Patent Document 2: JP 2012-111726 A
Patent Document 3: JP 2007-145722 A
Patent Document 4: JP 2013-199453 A

SUMMARY OF THE INVENTION

Problems to be Solved by the Invention

As mentioned above, conventional oil-in-water emulsion sunscreen cosmetics have the problem that the oil content must be increased in order to stably blend ultraviolet absorbing agents and ultraviolet scattering agents to achieve a high SPF, and this results in loss of the fresh sensation of use characteristic of oil-in-water emulsions, while conversely, if the sensation of use is prioritized, the amount of oil should be so lesser that the ultraviolet protection capability is limited.

Therefore, the present invention has the purpose of offering an oil-in-water cosmetic emulsion that has a distinctively fresh sensation of use, collapsing as if melting when applied to the skin, while also having excellent ultraviolet protection capability.

Means for Solving the Problems

The present inventors performed diligent research in order to solve the above-mentioned problems, as a result of which they discovered that a high SPF can be achieved while maintaining a distinctively fresh feeling in use, by using a hydrophobically modified cellulose derivative having a specific structure as the emulsifier, including an ultraviolet absorbing agent and a hydrophobically treated ultraviolet scattering agent in the oil phase (inner phase), and adding a thickener having low salinity tolerance to the water phase (outer phase), thereby completing the present invention.

In other words, the present invention provides an oil-in-water emulsion cosmetic characterized by comprising:
(A) 0.05 to 1% by mass of a hydrophobically modified alkyl cellulose;
(B) 5 to 40% by mass of an oil component;
(C) 2.5 to 30% by mass of an ultraviolet scattering agent having a hydrophobic surface; and
(D) a water phase thickener having low salinity tolerance;
wherein the (C) ultraviolet scattering agent is dispersed in the oil phase.

Effects of the Invention

The oil-in-water emulsion cosmetic of the present invention, due to using a hydrophobically modified alkyl cellulose and blending a thickener into the water phase, is capable of achieving a high SPF by blending high quantities of an ultraviolet absorbing agent and an ultraviolet scattering agent while suppressing the total oil content. Furthermore, in the present invention, the water phase contains a thickener having low salinity tolerance, the use of which has been conventionally avoided as adversely affecting emulsion stability, thereby obtaining an excellent feeling in use providing a Distinctive fresh feeling as if melting upon application to the skin.

In the present description, "Distinctive fresh feeling" refers to an extremely refreshing sensation wherein, upon application of the cosmetic to the skin using the fingers, there is a sudden loss of viscosity and collapsing sensation as if melting, while simultaneously spreading over the skin.

MODES FOR CARRYING OUT THE INVENTION

Herebelow, the present invention will be explained in detail.

The oil-in-water emulsion cosmetic (hereinafter referred to simply as "emulsion cosmetic") of the present invention comprises (A) a hydrophobically modified alkyl cellulose, (B) an oil component; (C) an ultraviolet scattering agent having a hydrophobic surface; and (D) a water phase thickener having low salinity tolerance.

The (A) hydrophobically modified alkyl cellulose used in the present invention refers to an alkyl cellulose that has been hydrophobically modified by an alkyl group having 14 to 22 carbon atoms. This hydrophobically modified alkyl cellulose is a compound having a long-chain alkyl group, which is a hydrophobic group, introduced to a water-soluble cellulose ether derivative, represented by the following general formula (I):

[Chemical Formula 1]

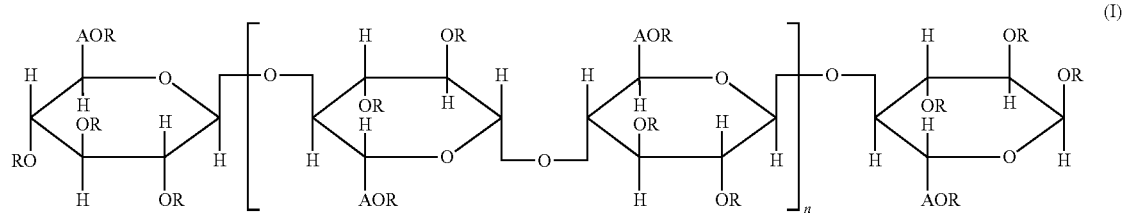

wherein R may be identical or different, and is one or more groups selected from the group consisting of a hydrogen atom, an alkyl group having 1 to 4 carbon atoms, the group —[CH$_2$CH(CH$_3$)O]$_m$—H (wherein m is an integer of 1 to 5, preferably 1 to 3), the group —CH$_2$CH$_2$OH, and the group —CH$_2$CH(OH)CH$_2$OR' (wherein R' is an alkyl group having 14 to 22 carbon atoms), but always including the group —CH$_2$CH(OH)CH$_2$OR'; and A is the group —(CH$_2$)$_q$— (wherein q is an integer of 1 to 3, preferably 1), and n is an integer of 100 to 10000, preferably 500 to 5000.

The method for producing the hydrophobically modified alkyl cellulose of the above formula (I) may generally involve bringing a water-soluble cellulose ether derivative that is to form the base, specifically methyl cellulose (wherein R is a hydrogen atom or a methyl group), ethyl cellulose (wherein R is a hydrogen atom or an ethyl group), propyl cellulose (wherein R is a hydrogen atom or a propyl group), butyl cellulose (wherein R is a hydrogen atom or a butyl group), hydroxypropyl cellulose [wherein R is a hydrogen atom or a hydroxypropyl group (the group —[CH$_2$CH(CH$_3$)O]$_m$—H (wherein m is an integer of 1 to 5, preferably 1 to 3))] or hydroxypropyl methylcellulose (wherein R is a hydrogen atom, a methyl group or a hydroxypropyl group (as defined above)), into contact with a compound for introducing a long-chain alkyl group having 14 to 22 carbon atoms, specifically the long-chain alkylglycidyl ether of the following formula (II), in the presence of an alkali catalyst.

[Chemical Formula 2]

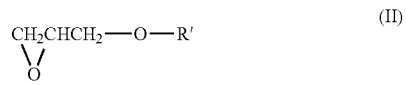

wherein R' is an alkyl group having 14 to 22 carbon atoms.

The amount of the group —CH$_2$CH(OH)CH$_2$OR' introduced in the hydrophobically modified alkyl cellulose of the present invention should preferably be about 0.1 to 5.0% by mass with respect to the entire hydrophobically modified alkyl cellulose. In order to obtain this content, the compound should be produced by appropriately choosing the molar ratio, reaction time, and type of alkali catalyst when reacting the water-soluble cellulose ester derivative with the long-chain alkylglycidyl ether. The above-mentioned reaction may be followed by a purification process such as neutralization, filtration, washing, drying and sifting of the reactant.

Among the above-mentioned water-soluble cellulose ether derivatives, it is particularly preferable to select hydroxypropyl methylcellulose (as a result, the R in formula (I) will be one of four possible groups, namely a hydrogen atom, a methyl group, the group —[CH$_2$CH(CH$_3$)O]$_m$H or the group —CH$_2$CH(OH)CH$_2$OR', the q in group A will be 1, and A will be a methylene group).

Furthermore, R' in the long-chain alkylglycidyl ether of formula (II) will be an alkyl group having 14 to 22 carbon atoms, preferably an alkyl group having 14 to 20 carbon atoms, and more preferably a stearyl group having 18 carbon atoms (—C$_{18}$H$_{37}$). If the number of carbon atoms in the alkyl group R' is less than 14 or at least 23, then the emulsion stability due to the resulting hydrophobically modified alkyl cellulose will be insufficient.

The weight-average molecular weight of the hydrophobically modified alkyl cellulose is preferably 100,000 to 1,000,000, more preferably 300,000 to 800,000, and even more preferably 550,000 to 750,000.

In the present invention, the use of stearoxy hydroxypropyl cellulose as the hydrophobically modified alkyl cellulose is most preferred, and commercially available products may be used. Examples include Sangelose 90 L (label name: hydrophobic hydroxypropyl methylcellulose; product of Daido Chemical Corp.), Natrosol Plus 330cs (product of Ashland Inc.) and Polysurf 67cs (product of Ashland Inc.).

The blended amount of the hydrophobically modified alkyl cellulose (A) in the emulsion cosmetic of the present invention is 0.05 to 1% by mass, preferably 0.1 to 0.5% by mass, more preferably 0.1 to 0.3% by mass. At less than 0.05% by mass, sufficient emulsion stability cannot be obtained, and even if more than 1% by mass is added, further increases in effects are difficult to obtain.

The (B) oil component in the emulsion cosmetic of the present invention can be one or more types selected from the oil components that are normally used in cosmetics and the like.

The blended amount of the (B) oil component is 5 to 40% by mass, preferably 10 to 40% by mass, more preferably 20 to 35% by mass with respect to the emulsion cosmetic.

In the emulsion cosmetic of the present invention, by using a polar oil as at least 55% by mass, preferably at least 60% by mass, more preferably at least 70% by mass, and even more preferably at least 80% by mass of the oil component (B), the emulsion stability can be further improved. The upper limit of the proportion of the oil component constituted by polar oils is not particularly limited, and for example, polar oils can constitute 90% or more, and the oil component may even be 100% polar oils.

The "polar oils" in the present specification are not particularly limited as long as they are of high polarity among the oils generally used in cosmetics, and for example, those with a dielectric constant of about 5 or more, preferably about 10 or more, can be favorably used.

Representative examples of polar oils that can be used in the emulsion cosmetic of the present invention include ester oils and ultraviolet absorbing agents. Additionally, due to the inclusion of a higher quantity of polar oils than conventional emulsion cosmetics, for example, high-polarity fragrances and the like may be stably blended.

Specific examples of ester oils that are suitable for the emulsion cosmetic of the present invention include tripropylene glycol dineopentanoate, isononyl isononanoate, isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxystearate, cetyl ethylhexanoate, ethylene glycol di-2-ethylhexanoate, dipentaerythritol fatty acid ester, N-alkylglycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythrityl tetra-2-ethylhexanoate, triethylhexanoin (glycerin tri-2-ethylhexanoate), glycerin trioctanoate, glycerin triisopalmitate, trimethylolpropane triisostearate, cetyl 2-ethylhexanoate, 2-ethylhexyl palmitate, glycerin trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamate-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate and triethyl citrate.

Examples of ultraviolet absorbing agents include a wide range of high-polarity oil-based ultraviolet absorbing agents that are commonly used in cosmetics, but not particular limited. Examples include benzoic acid derivatives, salicylic acid derivatives, cinnamic acid derivatives, dibenzoylmethane derivatives, β,β-diphenylacrylate derivatives, benzophenone derivatives, benzylidene camphor derivatives, phenylbenzoimidazole derivatives, triazine derivatives, phenylbenzotriazole derivatives, anthranil derivatives, imidazoline derivatives, benzalmalonate derivatives and 4,4-diaryl butadiene derivatives. Specific examples and product names will be listed below, but not limited thereto.

Examples of benzoic acid derivatives include ethyl para-aminobenzoate (PABA), ethyl-dihydroxypropyl PABA, ethylhexyl-dimethyl PABA (e.g. "Escalol 507"; ISP), glyceryl PABA, PEG-25-PABA (e.g. "Uvinul P25"; BASF) and hexyl diethylamino hydroxybenzoyl benzoate (e.g. "Uvinul A Plus").

Examples of salicylic acid derivatives include homosalate ("Eusolex HMS"; Rona/EM Industries), ethylhexyl salicylate (e.g. "Neo Heliopan OS"; Haarmann & Reimer), dipropylene glycol salicylate (e.g. "Dipsal"; Scher) and TEA salicylate (e.g. "Neo Heliopan TS"; Haarmann & Reimer).

Examples of cinnamic acid derivatives include octylmethoxy cinnamate or ethylhexyl methoxycinnamate (e.g. "Parsol MCX"; Hoffman-La Roche), isopropyl methoxycinnamate, isoamyl methoxycinnamate (e.g. "Neo Heliopan E1000"; Haarmaan & Reimer), cinnoxate, DEA methoxycinnamate, di isopropyl methylcinnamate, glyceryl ethylhexanoate dimethoxycinnamate, and di-(2-ethylhexyl)-4'-methoxybenzalmalonate.

Examples of dibenzoyl methane derivatives include 4-tert-butyl-4'-methoxy dibenzoyl methane (e.g. "Parsol 1789").

Examples of β,β-diphenyl acrylate derivatives include octocrylene (e.g. "Uvinul N539"; BASF).

Examples of benzophenone derivatives include benzophenone-1 (e.g. "Uvinul 400"; BASF), benzophenone-2 (e.g. "Uvinul D50"; BASF), benzophenone-3 or oxybenzone (e.g. "Uvinul M40"; BASF), benzophenone-4 (e.g. "Uvinul MS40"; BASF), benzophenone-5, benzophenone-6 (e.g. "Helisorb 11"; Norquay), benzophenone-8 (e.g. "Spectra-Sorb UV-24"; American Cyanamid), benzophenone-9 (e.g. "Uvinul DS-49"; BASF) and benzophenone-12.

Examples of benzylidene camphor derivatives include 3-benzylidene camphor (e.g. "Mexoryl SD"; Chimex), 4-methylbenzylidene camphor, benzylidene camphor sulfonic acid (e.g., "Mexoryl SL"; Chimex), camphor benzalkonium methosulfate (e.g. "Mexoryl SO"; Chimex), terephthalylidene dicamphor sulfonic acid (e.g. "Mexoryl SX"; Chimex) and polyacrylamide methylbenzylidene camphor (e.g. "Mexoryl SW"; Chimex).

Examples of phenylbenzoimidazole derivatives include phenylbenzoimidazole sulfonic acid (e.g. "Eusolex 232"; Merck) and disodium phenyldibenzimidazole tetrasulfonate (e.g. "Neo Heliopan AP"; Haarmann & Reimer).

Examples of triazine derivatives include anisotriazine (e.g. "Tinosorb S"; Ciba Specialty Chemicals), ethylhexyl triazone (e.g. "Uvinul T150"; BASF), diethylhexyl butamido triazone (e.g. "Uvasorb HEB"; Sigma 3V) and 2,4,6-tris(diisobutyl-4'-aminobenzalmalonate)-s-triazine.

Examples of phenylbenzotriazole derivatives include drometrizole trisiloxane (e.g. "Silatrizole"; Rhodia Chimie) and methylene bis(benzotriazolyl tetramethylbutyl phenol) (e.g. "Tinosorb M" (Ciba Specialty Chemicals)).

Examples of anthranil derivatives include menthyl anthranilate (e.g. "Neo Heliopan MA"; Haarmann & Reimer).

Examples of imidazoline derivatives include ethylhexyl dimethoxybenzylidene dioxoimidazoline propionate.

Examples of benzalmalonate derivatives include polyorganosiloxanes having a benzalmalonate functional group (e.g. Polysilicone-15; "Parsol SLX"; DSM Nutrition Japan).

Examples of 4,4-diarylbutadiene derivatives include 1,1-dicarboxy (2,2'-dimethylpropyl)-4,4-diphenylbutadiene.

Other oils (hereinafter referred to also as "non-polar oils") that can be added together with the aforementioned polar oils include low-polarity oils among the oils that are generally added to cosmetics, for example, one or more oils selected from oils having a dielectric constant of about 5 or less.

The blended amount of the ultraviolet absorbing agent contained in the polar oil, for example, should be at least 40% by mass, preferably at least 50% by mass, and more preferably at least 60% by mass with respect to the polar oil.

The blended amount of the ultraviolet absorbing agent with respect to the entire emulsion cosmetic should be 5 to 25% by mass, preferably 8 to 23% by mass, and more preferably 10 to 20% by mass.

While the non-polar oil blended in the emulsion cosmetic of the present invention is not particularly limited, it should preferably be selected from the group consisting of volatile or non-volatile silicone oils and hydrocarbon oils.

Specific examples include linear silicone oils such as polydimethylsiloxane, methylphenylpolysiloxane and methyl hydrogen polysiloxane, cyclic silicone oils such as octamethylcyclotetrasiloxane, decamethylcyclopentasiloxane and dodecamethylcyclohexasiloxane, and hydrocarbon oils such as decane, dodecane, isododecane, isohexadecane, liquid paraffin, squalane, squalene and paraffin.

As the base material for the (C) ultraviolet scattering agent having a hydrophobic surface in the emulsion cosmetic of the present invention, a zinc oxide or titanium oxide powder is preferably used.

The zinc oxides and titanium oxides used in the present invention are not particularly limited, and can be appropriately selected from those normally used in cosmetics.

The ultraviolet scattering agent (C) used in the present invention is an ultraviolet scattering agent having a hydrophobic surface, obtained by hydrophobically treating the surface of a base material such as zinc oxide or titanium oxide.

The method of hydrophobic treatment of the surface may be a silicone treatment using methyl hydrogen polysiloxane, methylpolysiloxane or the like; a fluorine treatment using a perfluoroalkyl phosphoric acid ester, a perfuoroalcohol or the like; an amino acid treatment using N-acylglutamic acid or the like; a lecithin treatment; a metal soap treatment; a fatty acid treatment; or an alkyl phosphoric acid ester treatment.

The blended amount of the (C) ultraviolet scattering agent having a hydrophobic surface in the emulsion cosmetic of the present invention is 2.5 to 30% by mass, preferably 3 to 30% by mass and more preferably 4 to 20% by mass. When the blended amount is less than 2.5% by mass, it is difficult to obtain SPF values that are higher than conventional examples, and the Distinctive fresh feel at the time of application tends not to be obtained. On the other hand, when added in excess of 30% by mass, there are cases in which the emulsion stability and usability are reduced.

The (D) water phase thickener having low salinity tolerance in the present invention is a thickener having the function of thickening the water phase, which undergoes a reduction in viscosity due to the presence of an electrolyte at a concentration in a range that is normally blended in cosmetics. Such thickeners having low salinity tolerance are selected from among water-soluble thickeners that are conventionally blended in cosmetics for the purpose of adjusting the viscosity of the water phase.

Specific examples include vinyl polymers such as polyvinyl alcohol, polyvinyl acetate, polyvinyl methyl ether, polyvinyl pyrrolidone, copolymers of vinyl pyrrolidone and vinyl acetate, and carboxyvinyl polymers; and acrylic polymers such as sodium polyacrylate, poly ethyl acrylate, alkanolamine polyacrylate, copolymers of alkyl methacrylate and dimethylaminoethyl methacrylate, poly-2-acrylamido-2-methylpropane sulfonic acid, polymethacryloyloxy trimethylammonium, (ammonium acryloyldimethyl taurate/VP) copolymers, and (dimethylacrylamide/sodium acryloyldimethyl taurate) crosspolymers.

However, even among thickeners having low salinity tolerance (in which viscosity decreases occur due to increases in electrolyte concentration), compared to thickeners of the type that thicken by entanglement of polymer chains, the use of thickeners of the type that form a water-swellable microgel in the water phase and thicken due to friction between the swollen microgel particles is preferred because they can further suppress slipperiness when rubbing the cosmetic into the skin. This is due to the fact that hydrophobically modified alkyl cellulose which is added as an emulsifier also has a thickening function based on entanglement of polymer chains, so that the further addition of a thickener of the type that thickens due to the same mechanism will further boost the thickening function and cause slipperiness.

The blended amount of the (D) water phase thickener having low salt tolerance in the emulsion cosmetic of the present invention is 0.05 to 3% by mass, preferably 0.1 to 2% by mass, and more preferably 0.15 to 1% by mass. If less than 0.05% by mass, the functions as a thickener (viscosity adjustment and emulsion stabilization) cannot be achieved, and the Distinctive fresh feel cannot be obtained at the time of application. If more than 3% by mass is added, then stickiness or slipperiness can occur.

The emulsion cosmetic of the present invention may, in addition to the above-described essential components (A) to (D), include various components that are normally blended in cosmetics, within a range not inhibiting the effects of the present invention. Specific examples include, but are not limited to, glycols such as propylene glycol, dipropylene glycol, 1,3-butylene glycol, 1,4-butylene glycol, diethylene glycol, triethylene glycol and polyethylene glycol; glycerins such as glycerin, diglycerin and polyglycerin; sugar alcohols such as sorbitol, mannitol, maltitol, xylitol and erythritol; sugars such as fructose, glucose, galactose, maltose, lactose and trehalose; natural pigments such as chlorophyll and β-carotene; vegetable polymers such as gum arabic, tragacanth gum, galactan, guar gum, carob gum, karaya gum, gellan gum and carrageenan; microbial polymers such as xanthan gum, dextran, succinoglucan and pullulan; animal polymers such as collagen, casein, albumin and gelatin; starch polymers such as carboxymethyl starch and methylhydroxypropyl starch; cellulose polymers such as methyl cellulose, ethyl cellulose, methylhydroxypropyl cellulose, hydroxyethylcellulose, sodium cellulose sulfate, hydroxypropyl cellulose, sodium carboxymethylcellulose and crystalline cellulose; alginic acid polymers such as sodium alginate and propylene glycol esters of alginic acid; other thickeners; vitamins such as magnesium ascorbyl phosphate, glucoside ascorbate, vitamin $B_6$ hydrochloride and pantothenyl ethyl ether; chemical agents such as germicides, antiphlogistic agents, preservatives, vegetable extracts, amino acids and algiefacients; lower alcohols such as ethanol and isopropyl alcohol; aromatic alcohols such as phenoxyethanol and benzyl alcohol; and surfactants.

The emulsion cosmetic of the present invention, while being an oil-in-water emulsion composition, due to the use of hydrophobically modified alkyl cellulose as an emulsifier, allows a higher amount of polar oils including an ultraviolet absorbing agent and an ultraviolet scattering agent having a hydrophobic surface to be blended into the inner phase (oil phase) than in conventional oil-in-water cosmetics, thereby achieving excellent ultraviolet protection capability. Furthermore, it provides the surprising effect of improving the emulsion stability as a result of setting the proportion of polar oils in the oil phase to at least 55% by mass, even though they were conventionally thought to be a cause of destabilization.

On the other hand, since hydrophobically modified alkyl cellulose has a suitable level of emulsifying power, the ultraviolet scattering agent blended in the inner phase (oil phase) can easily interact with the outer phase (water phase), so that when applied to the skin in particular, electrolytes (such as the ultraviolet scattering agent) released from the inner phase will contact the thickener in the water phase and cause a sudden drop in viscosity, thereby providing a Distinctive fresh feeling as if melting. Therefore, the emulsion cosmetic of the present invention preferably does not substantially contain any emulsifiers other than hydrophobically modified alkyl cellulose, particularly emulsifiers having strong emulsifying effect. When blending other emulsifiers, they should preferably be added in an amount of 3% by mass or less, or about 1% by mass or less.

The emulsion cosmetic of the present invention can be prepared according to methods that are normally used in oil-in-water emulsion cosmetics. In other words, it can be prepared by separately mixing together the water phase components and the oil phase components, then emulsifying by adding the oil phase components to the water phase components while stirring.

The emulsion cosmetic of the present invention is not particularly limited, but should preferably have an inner phase (oil phase) with an average particles size of normally about 15 μm or less.

EXAMPLES

Herebelow, the present invention will be explained in further detail by providing specific examples, but these do not in any way limit the technical scope of the present invention.

In the following examples etc., the amounts are in % by mass where not otherwise specially noted.

Oil-in-water emulsion cosmetics were prepared with the formulations shown in below-indicated Table 1 to Table 5, and their properties were evaluated in accordance with the below-described evaluation methods and evaluation standards. The results thereof are also shown in the tables.

1. Evaluation Method of Feeling in Use

Samples of the examples and the comparative examples were actually used by five expert panelists and evaluated for their feeling in use. The results were evaluated into five grades in accordance with the scoring criteria indicated below, and then judged on the basis of the evaluation criteria indicated below in accordance with their total scores.

Evaluation Category
(1) Distinctive Fresh Feeling in Use
Whether, as defined above, upon application to the skin, there is a sudden loss of viscosity and a sensation of collapse, and a sensation of freshness spreading over the skin.
(2) Slipperiness When Rubbed In
Whether there is no sensation of slipperiness when the applied cosmetic is rubbed into the skin.

Scoring Criteria
5: very good
4: good
3: average
2: poor
1: very poor

Evaluation Criteria
A: total of 20 points or more
B: total of 15 to 19 points
C: total of 14 points or less 2. Emulsion Stability Two screw-top vials (50 ml) were filled with a sample, and let stand for 2 weeks in a thermostatic bath at 0° C. or 50° C. The viscosity change was measured using a rotary viscometer (Vismetron rotary viscometer) before and after letting stand, and observations of the emulsified particles and appearance were made.

Evaluation Criteria
A: No viscosity loss observed for either temperature standard 0° C. or 50° C., and no problems in emulsified particles or appearance.
B: Some viscosity loss, increased size of emulsified particles or change in appearance observed in one of the temperature standards.
C: Some viscosity loss, increased size of emulsified particles or change in appearance observed in both temperature standards.
D: Significant viscosity loss, increased size of emulsified particles or change in appearance observed in one of the temperature standards.
E: Significant viscosity loss, increased size of emulsified particles or change in appearance observed in both temperature standards.

TABLE 1

| Class | Component Name | Ex. 1 | Ex. 2 | Ex. 3 | Ex. 4 | Ex. 5 | Comp. Ex. 1 |
|---|---|---|---|---|---|---|---|
| Base | Ion exchanged water | 64.5 | 64.5 | 64.5 | 67.5 | 68.5 | 70.5 |
|  | Ethanol | — | — | — | — | — | — |
| Emulsifier/ Thickener | Stearoxyhydroxypropyl methylcellulose | 0.2 | 0.2 | 0.2 | 0.2 | 0.2 | 0.2 |
| Ultraviolet Scattering Agent | Silicone-treated zinc oxide | 7 | — | — | 4 | 3 | 1 |
|  | Silica-coated zinc oxide | — | 7 | — | — | — | — |
|  | Silicone-treated titanium oxide | — | — | 7 | — | — | — |
| Non-polar Oil | Isododecane | 2 | 2 | 2 | 2 | 2 | 2 |
| Polar Oil | Triethylhexanoin | — | — | — | — | — | — |
|  | Pentaerythrityl tetraethylhexanoate | — | — | — | — | — | — |
|  | Cetyl ethylhexanoate | 3 | 3 | 3 | 3 | 3 | 3 |

TABLE 1-continued

| Class | Component Name | Ex. 1 | Ex. 2 | Ex. 3 | Ex. 4 | Ex. 5 | Comp. Ex. 1 |
|---|---|---|---|---|---|---|---|
| Polar Oil (Ultraviolet Absorbing Agent) | Ethylhexyl methoxycinnamate | 10 | 10 | 10 | 10 | 10 | 10 |
| | Diethylaminohydroxybenzoyl hexyl benzoate | 2 | 2 | 2 | 2 | 2 | 2 |
| | Bis-ethylhexyloxyphenol methoxyphenyl triazine | 1 | 1 | 1 | 1 | 1 | 1 |
| Humectant | Butylene glycol | 10 | 10 | 10 | 10 | 10 | 10 |
| Thickener | (Dimethylacrylamide/sodium acryloyldimethyltaurate) crosspolymer | 0.3 | 0.3 | 0.3 | 0.3 | 0.3 | 0.3 |
| | Distinctive Fresh Feeling in Use | A | A | A | A | B | C |

According to the results shown in Table 1, the oil-in-water emulsion cosmetics (Examples 1 to 5) having hydrophobically modified alkyl cellulose as the emulsifier, containing a high-polarity ultraviolet absorbing agent and a hydrophobically surface-treated ultraviolet scattering agent in the oil phase, and having a water phase thickened with a thickener having low salt tolerance resulted in a Distinctive fresh feeling in use at the time of application, while Comparative Example 1 for which the blended amount of the ultraviolet scattering agent did not satisfy the designated values was insufficient to lower the viscosity of the water phase and was not able to provide the desired feeling in use. An emulsion cosmetic having a water phase thickened with a thickener having high salt tolerance also was not able to achieve a Distinctive fresh feeling in use.

TABLE 2

| Class | Component Name | Ex. 6 | Ex. 7 | Ex. 8 |
|---|---|---|---|---|
| Base | Ion exchanged water | 62.5 | 62.5 | 67.3 |
| | Ethanol | — | — | — |
| Emulsifier/Thickener | Stearoxyhydroxypropyl methylcellulose | 0.2 | 0.2 | 0.2 |
| Ultraviolet Scattering Agent | Silicone-treated zinc oxide | 9 | 9 | 4 |
| Non-polar Oil | Isododecane | 2 | 2 | 2 |
| Polar Oil | Triethylhexanoin | — | — | — |
| | Pentaerythrityl tetraethylhexanoate | — | — | — |
| | Cetyl ethylhexanoate | 3 | 3 | 3 |
| Polar Oil (Ultraviolet Absorbing Agent) | Ethylhexyl methoxycinnamate | 10 | 10 | 10 |
| | Diethylaminohydroxybenzoyl hexyl benzoate | 2 | 2 | 2 |
| | Bis-ethylhexyloxyphenol methoxyphenyl triazine | 1 | 1 | 1 |
| Humectant | Butylene glycol | 10 | 10 | 10 |
| Thickener | (Dimethylacrylamide/sodium acryloyldimethyltaurate) crosspolymer | 0.3 | — | — |
| | (Ammonium acryloyldimethyl taurate/VP) copolymer | — | 0.3 | — |
| | Carbomer | — | — | 0.5 |
| | Distinctive Fresh Feeling in Use | A | A | A |
| | Slipperiness When Rubbed In | A | A | B |

The Distinctive Fresh Feeling in Use obtained in Table 1 (Examples 1 to 5) was achieved even when changing the type of thickener having low salinity tolerance blended in the water phase (Examples 6 and 7). However, in Example 8 using a thickener (carbomer) of the type that thickens by entanglement of molecules, some slipperiness was felt when rubbing the cosmetic into the skin.

TABLE 3

| Class | Component Name | Ex. 6 | Ex. 9 | Ex. 10 | Ex. 11 |
|---|---|---|---|---|---|
| Base | Ion exchanged water | 62.5 | 50.5 | 50.5 | 50.5 |
| | Ethanol | — | — | — | 12 |
| Emulsifier/Thickener | Stearoxyhydroxypropyl methylcellulose | 0.2 | 0.2 | 0.2 | 0.2 |
| Ultraviolet Scattering Agent | Silicone-treated zinc oxide | 9 | 9 | 9 | 9 |
| Non-polar Oil | Isododecane | 2 | 2 | 2 | 2 |
| Polar Oil | Triethylhexanoin | — | 12 | — | — |
| | Pentaerythrityl tetraethylhexanoate | — | — | 12 | — |
| | Cetyl ethylhexanoate | 3 | 3 | 3 | 3 |

TABLE 3-continued

| Class | Component Name | Ex. 6 | Ex. 9 | Ex. 10 | Ex. 11 |
|---|---|---|---|---|---|
| Polar Oil (Ultraviolet Absorbing Agent) | Ethylhexyl methoxycinnamate | 10 | 10 | 10 | 10 |
| | Diethylaminohydroxybenzoyl hexyl benzoate | 2 | 2 | 2 | 2 |
| | Bis-ethylhexyloxyphenol methoxyphenyl triazine | 1 | 1 | 1 | 1 |
| Humectant | Butylene glycol | 10 | 10 | 10 | 10 |
| Thickener | (Dimethylacrylamide/sodium acryloyldimethyltaurate) crosspolymer | 0.3 | 0.3 | 0.3 | 0.3 |
| | Polar Oil/Total Oil Content (%) | 88.89 | 93.33 | 93.33 | 88.89 |
| | Distinctive Fresh Feeling in Use | A | A | A | A |
| | Emulsion Stability | A | A | A | A |

Examples 9 to 11 in which the polar oil added in Example 6 was replaced by other polar oils also achieved a Distinctive feeling in use like that of Example 6, and also excelled in emulsion stability.

TABLE 4

| Class | Component Name | Ex. 12 | Ex. 13 | Ex. 14 | Ex. 15 |
|---|---|---|---|---|---|
| Base | Ion exchanged water | 50.5 | 50.5 | 50.5 | 50.45 |
| | Ethanol | — | — | — | — |
| Emulsifier/Thickener | Stearoxyhydroxypropyl methylcellulose | 0.2 | 0.2 | 0.2 | 0.2 |
| Ultraviolet Scattering Agent | Silicone-treated zinc oxide | 9 | 9 | 9 | 9 |
| Non-polar Oil | Isododecane | 3 | 15 | 3 | 3 |
| | Cyclomethicone | 12 | — | — | 12 |
| | Dimethicone | — | — | 12 | — |
| Polar Oil | Cetyl ethylhexanoate | 2 | 2 | 2 | 2 |
| Polar Oil (Ultraviolet Absorbing Agent) | Ethylhexyl methoxycinnamate | 10 | 10 | 10 | 10 |
| | Diethylaminohydroxybenzoyl hexyl benzoate | 2 | 2 | 2 | 2 |
| | Bis-ethylhexyloxyphenol methoxyphenyl triazine | 1 | 1 | 1 | 1 |
| Humectant | Butylene glycol | 10 | 10 | 10 | 10 |
| Thickener | (Dimethylacrylamide/sodium acryloyldimethyltaurate) crosspolymer | 0.3 | 0.3 | 0.3 | 0.3 |
| | Trisodium EDTA | — | — | — | 0.05 |
| | Polar Oil/Total Oil Content (%) | 50.00 | 50.00 | 50.00 | 50.00 |
| | Distinctive Fresh Feeling in Use | A | A | A | B |
| | Emulsion Stability | C | C | C | A |

In Examples 1 to 11 shown in Tables 1 to 3, the proportion of polar oils within the total oil content exceeded 55%, and they exhibited very good emulsion stability, whereas in Examples 12 to 14 in which the proportion of polar oils in the total oil content was less than 55%, the emulsion stability was somewhat reduced (though it was of a level that presented no problems in actual use). In Example 15 wherein the chelating agent trisodium EDTA was added to Example 12, the emulsion stability was improved by the addition of the chelating agent, but a tendency for the Distinctive fresh feeling in use to be somewhat reduced was observed. This can be considered to be due to a portion of the electrolytes being captured by the chelating agent so as to somewhat inhibit the sudden loss in viscosity. Therefore, it appears to be preferable to hold the amount of chelating agent to be added to the emulsion cosmetic of the present invention to a minimum.

TABLE 5

| Class | Component Name | Ex. 16 | Ex. 17 | Ex. 18 | Ex. 19 |
|---|---|---|---|---|---|
| Base | Ion exchanged water | 50.5 | 50.5 | 50.5 | 50.5 |
| | Ethanol | 12 | 12 | 12 | 12 |
| Emulsifier/Thickener | Stearoxyhydroxypropyl methylcellulose | 0.2 | 0.2 | 0.2 | 0.2 |
| Ultraviolet Scattering Agent | Fatty acid-treated zinc oxide | 9 | — | — | — |
| | Silica-coated zinc oxide | — | 9 | — | — |

TABLE 5-continued

| Class | Component Name | Ex. 16 | Ex. 17 | Ex. 18 | Ex. 19 |
|---|---|---|---|---|---|
| | Silicone-treated titanium oxide | — | — | 9 | — |
| | Aluminum stearate-treated titanium oxide | — | — | — | 9 |
| Non-polar Oil | Isododecane | 3 | 3 | 3 | 3 |
| Polar Oil | Cetyl ethylhexanoate | 2 | 2 | 2 | 2 |
| Polar Oil (Ultraviolet Absorbing Agent) | Ethylhexyl methoxycinnamate | 10 | 10 | 10 | 10 |
| | Diethylaminohydroxybenzoyl hexyl benzoate | 2 | 2 | 2 | 2 |
| | Bis-ethylhexyloxyphenol methoxyphenyl triazine | 1 | 1 | 1 | 1 |
| Humectant | Butylene glycol | 10 | 10 | 10 | 10 |
| Thickener | (Dimethylacrylamide/sodium acryloyldimethyltaurate) crosspolymer | 0.3 | 0.3 | 0.3 | 0.3 |
| | Polar Oil/Total Oil Content (%) | 83.33 | 83.33 | 83.33 | 83.33 |
| | Distinctive Fresh Feeling in Use | A | A | A | A |
| | Emulsion Stability | A | A | A | A |

According to the results shown in Table 5, Examples 16 to 19, using a hydrophobically modified alkyl cellulose as the emulsifier, having a water phase thickened with a thickener having low salt tolerance, and having a polar oil proportion of at least 55% by mass in the oil phase, were further confirmed to obtain a Distinctive fresh feeling in use regardless of what kinds of surface treating agents and ultraviolet scattering agents having a hydrophobic surface were added to the oil phase, and to also have very good emulsion stability.

Example 20

An oil-in-water emulsion sunscreen cosmetic was prepared with the composition shown below. The resulting cosmetic provided a Distinctive fresh feel as if melting upon application to the skin, and had an SPF of about 55 after application.

| | Blended Components | Amount (% by mass) |
|---|---|---|
| (1) | Water | 48.95 |
| (2) | Ethanol | 10.00 |
| (3) | Zinc oxide | 9.30 |
| (4) | Butylene glycol | 8.00 |
| (5) | Glycerin | 2.00 |
| (6) | Polybutylene glycol/PPG-9/1 copolymer | 2.00 |
| (7) | Stearoxyhydroxypropyl methylcellulose | 0.20 |
| (8) | Ethylhexyl methoxycinnamate | 10.00 |
| (9) | Potysilicone-15 | 2.00 |
| (10) | Diethylaminohydroxybenzoyl hexyl benzoate | 2.00 |
| (11) | Bis-ethylhexyloxyphenol methoxyphenyl triazine | 1.50 |
| (12) | Cetyl ethylhexanoate | 3.00 |
| (13) | Triethoxycaprylylsilane | 0.70 |
| (14) | (Dimethylacrylamide/sodium acryloyldimethyltaurate) crosspolymer | 0.30 |
| (15) | Fragrance | 0.05 |

The invention claimed is:

1. A method of making an oil-in-water emulsion that provides a fresh feeling upon application to skin resulting from a sudden loss of viscosity upon application to the skin, the method comprising emulsifying
   (a) 5 to 40% by mass of an oil component, wherein the oil component comprises a combination of a polar oil and a non-polar oil, wherein at least 55% by mass of the oil component is constituted by the polar oil;
   (b) 0.05 to 1% by mass of an emulsifier wherein the emulsifier is a hydrophobically modified alkyl cellulose;
   (c) 3.0 to 30% by mass of an ultraviolet scattering agent having a hydrophobic surface, wherein the ultraviolet scattering agent is dispersed in the oil component; and
   (d) 0.15 to 1% by mass of a water phase thickener selected from the group consisting of polyvinyl alcohol, polyvinyl acetate, polyvinyl methyl ether, polyvinyl pyrrolidone, copolymers of vinyl pyrrolidone and vinyl acetate, carboxyvinyl polymers, sodium polyacrylate, poly ethyl acrylate, alkanolamine polyacrylate, copolymers of alkyl methacrylate and dimethylaminoethyl methacrylate, poly-2-acrylamido-2-methylpropane sulfonic acid, polymethacryloyloxy trimethylammonium, (ammonium acryloyldimethyl taurate/VP) copolymers, and (dimethylacrylamide/sodium acryloyldimethyl taurate) crosspolymers;
   wherein if the oil-in-water emulsion comprises additional emulsifiers other than the hydrophobically modified alkyl cellulose, the additional emulsifiers are used in an amount of 1% by mass or less.

2. The method according to claim 1, wherein the hydrophobically modified alkyl cellulose is hydrophobic hydroxypropyl methylcellulose.

3. The method according to claim 1, wherein the water phase thickener is a thickener that forms a water-swellable microgel in the water phase.

4. The method according to claim 1, wherein the emulsion is a sunscreen cosmetic.

* * * * *